US008474458B1

(12) United States Patent
Yadven et al.

(10) Patent No.: US 8,474,458 B1
(45) Date of Patent: Jul. 2, 2013

(54) ERGONOMIC CHIN SUPPORT FOR MEDICAL HEADGEAR

(76) Inventors: Mitchell W. Yadven, Bradenton, FL (US); Michael Greco, Bethpage, NY (US)

(*) Notice: Subject to any disclaimer, the term of this patent is extended or adjusted under 35 U.S.C. 154(b) by 651 days.

(21) Appl. No.: 12/589,855

(22) Filed: Oct. 29, 2009

(51) Int. Cl.
*A61M 11/00* (2006.01)

(52) U.S. Cl.
USPC ............ 128/207.11; 128/200.24; 128/207.13; 128/206.28

(58) Field of Classification Search
USPC ............. 128/200.24, 200.28, 201.22, 201.23, 128/203.29, 205.25, 206.21, 206.24, 206.27, 128/206.28, 207.11, 207.13, 207.18, 207.17; 24/176
See application file for complete search history.

(56) References Cited

U.S. PATENT DOCUMENTS

| | | | | |
|---|---|---|---|---|
| 3,049,778 A | * | 8/1962 | Weckesser | 24/180 |
| 5,295,480 A | * | 3/1994 | Zemo | 128/207.17 |
| 5,361,416 A | * | 11/1994 | Petrie et al. | 2/171.2 |
| 6,526,978 B2 | * | 3/2003 | Dominguez | 128/207.14 |
| 6,981,503 B1 | * | 1/2006 | Shapiro | 128/845 |
| 7,500,480 B2 | * | 3/2009 | Matula et al. | 128/200.24 |

* cited by examiner

*Primary Examiner* — Steven Douglas
(74) *Attorney, Agent, or Firm* — Schwartz Law Firm, P.C.

(57) ABSTRACT

An ergonomic chin support is designed for use in combination with medical headgear. The headgear has flexible straps adapted for locating a ventilation interface on a patient. The ergonomic chin support comprises a generally arcuate and substantially rigid chin cradle. First and second substantially rigid extensions are formed at opposite ends of the chin cradle, and are adapted for being pulled by respective straps of the headgear to urge the chin cradle against the mandible of the patient. Retaining posts are provided for retaining the ergonomic chin support at a fixed location along respective lengths of the straps.

18 Claims, 3 Drawing Sheets

ERGONOMIC CHIN SUPPORT FOR MEDICAL HEADGEAR

TECHNICAL FIELD AND BACKGROUND

The present disclosure relates broadly and generally to the medical industry, and more particularly to an ergonomic chin support for use in combination with medical headgear. Such headgear is commonly worn by patients during noninvasive ventilation (and pressure support therapies) to locate and secure a patient interface, such as a nasal or nasal/oral ventilation mask. Noninvasive ventilation may be used to administer general anesthesia, and in the treatment of certain medical disorders, such as obstructive sleep apnea and congestive heart failure. When under general anesthesia, patients lose consciousness and are not arousable, even by painful stimulation. The ability to independently maintain ventilatory function is often impaired, and many patients require assistance in maintaining a patent airway.

An estimated 20 to 25 million anesthetics are administered annually in the United States. With those administered anesthetics, a large portion of spontaneously breathing, non-intubated patients may experience a loss of upper airway muscle tone allowing the tongue and epiglottis to fall back against the posterior pharyngeal wall causing the airway to obstruct. Current interventions that are carried out by the anesthesia care professional in relieving this type obstruction deems the insertion of an oral airway, nasopharyngeal airway, or a slight extension at the atlanto-occipital joint (chin up). With the insertion of an oral airway, awake or lightly anesthetized patients may cough or even develop a laryngospasm during the airway insertion if the laryngeal reflexes are intact. With the insertion of a nasopharyngeal airway, the risk the patient developing an epitaxis as a result of insertion trauma is increased leading to airway irritation, laryngospasm, or in deeply sedated patient's pulmonary aspiration.

There have been many cases reported of facial nerve damage caused by pressure of the anesthetist's fingers and the ascending ramus of the patient's mandible as a result of forward pressure in attempts to maintain a patent upper airway. Accordingly, there remains a need for an improved, non-invasive treatment method or devices that is effective in maintaining a patent airway, reducing or eliminate intra-operative apneic events, and/or other linked complications. In the exemplary embodiments discussed herein, the present device can be simply applied by the anesthesia care provider without interrupting the surgeon or the procedure, or requiring the help of other operating room personnel. With the exemplary devices of the present disclosure, the anesthetist will have two free hands to chart or perform other needed procedures during the case without having to dedicate one hand to the mandible for a chin-lift intervention. A constant, stable O2 saturation will be maintained as the chest wall moves up and down indicating a patent airway.

SUMMARY OF EXEMPLARY EMBODIMENTS

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

According to one exemplary embodiment, the disclosure comprises headgear in combination with an ergonomic chin support. The headgear has flexible straps adapted for locating a ventilation interface on a patient. The ergonomic chin support comprises a generally arcuate and substantially rigid chin cradle. First and second substantially rigid extensions are formed at opposite ends of the chin cradle, and are adapted for being pulled by respective straps of the headgear to urge the chin cradle against the mandible of the patient. Means are provided for retaining the ergonomic chin support at a fixed location along respective lengths of the straps.

The term "ergonomic" is defined broadly herein to mean having one or more design features intended to promote comfort and fit of the chin support in an area of the patient's chin and mandible.

According to another exemplary embodiment, a chin cushion is located on the chin cradle.

According to another exemplary embodiment, the chin cushion comprises a material selected from a group consisting of gel, silicone, foam, rubber, and combinations of these materials.

According to another exemplary embodiment, the first and second extensions comprise respective strap channels designed to receive respective flexible straps of the headgear.

According to another exemplary embodiment, the means for retaining comprise respective retention posts formed with the first and second extensions within the strap channels of the ergonomic chin support. The retention posts selectively mate with complementary indexing holes formed along respective lengths of the flexible straps. Alternatively, the means for retaining may comprise any other complementary retaining structure, such as hook and loop, snaps, friction (textured) surfaces, and the like.

According to another exemplary embodiment, the chin cradle and extensions are integrally-formed together as a single homogenous unit.

According to another exemplary embodiment, the first and second extensions are substantially co-linear.

According to another exemplary embodiment, the first and second extensions define respective closed strap slots receiving (therethrough) the flexible straps of the headgear, such that the ergonomic chin support is slidably disposed on respective lengths of the straps.

According to another exemplary embodiment, the flexible straps comprise respective enlarged end stops adapted for holding the ergonomic chin support onto the headgear.

In another exemplary embodiment, the disclosure comprises a method for maintaining a patent airway during noninvasive ventilation of a patient. The method includes locating a ventilation interface on the patient. The ventilation interface is secured using headgear comprising flexible straps. Using the flexible straps, an ergonomic chin support is pulled against the mandible of the patient. The ergonomic chin support is selectively retained at a fixed location along respective lengths of the flexible straps.

According to another exemplary embodiment, the step of selectively retaining comprises mating retention posts formed with the ergonomic chin support with complementary indexing holes formed with the flexible straps.

The exemplary chin support of the present disclosure may be used in combination with any headgear including (e.g.) a nasal cannula. In this implementation, complementary hook and loop fasteners (such as VELCRO®) or other appropriate means may be used to located and secure the chin support under the mandible of the patient.

BRIEF DESCRIPTION OF THE DRAWINGS

The description of exemplary embodiments proceeds in conjunction with the following drawings, in which.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
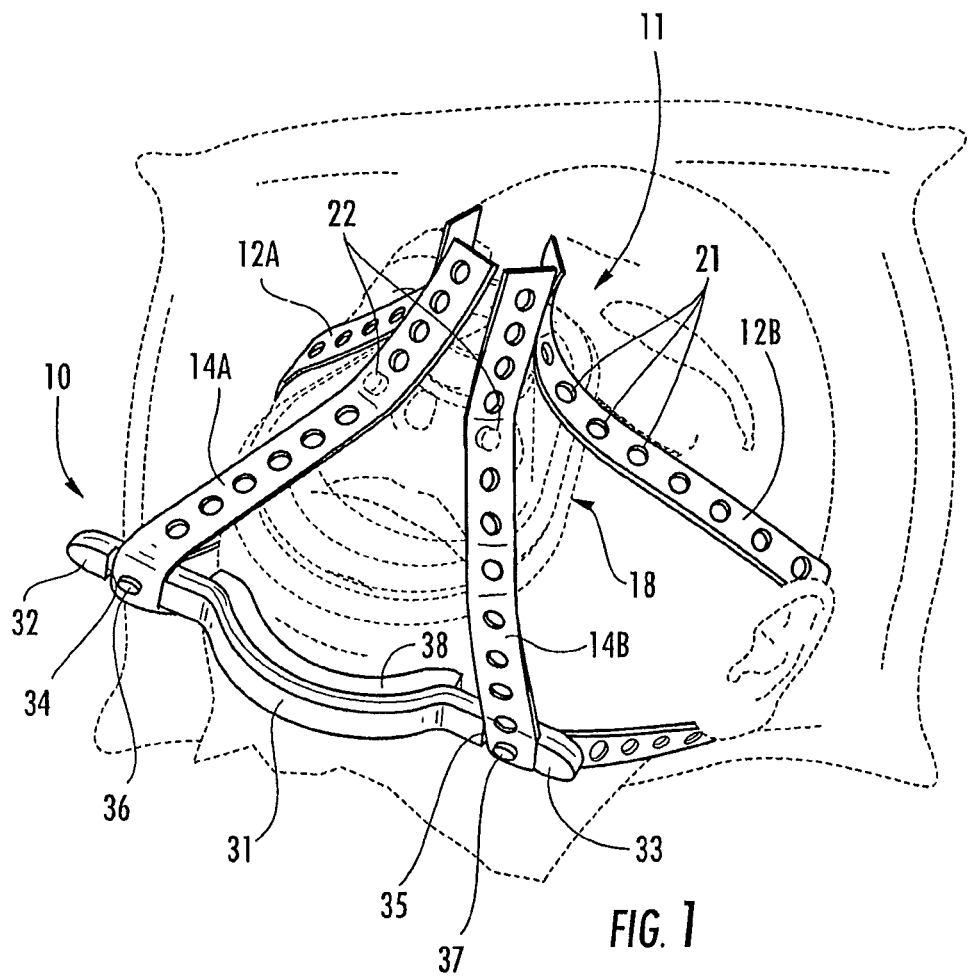
FIG. 1 is an environmental perspective view of an ergonomic chin support according to one exemplary embodiment of the present disclosure, and showing the ergonomic chin support used in combination with headgear and a noninvasive ventilation interface.

Referring now specifically to the drawings, an ergonomic chin support according to one exemplary embodiment of the present invention is illustrated in FIG. 1, and shown generally at reference numeral 10. In the exemplary implementation shown, the ergonomic chin support 10 is used in combination with headgear 11 comprising pairs of top and bottom flexible straps 12A, 12B and 14A, 14B. The flexible straps 12A, 12B, 14A, 14B are integrally formed with a perforated headpiece 15, and cooperate to properly locate and secure a nasal/oral ventilation mask 18 (or other noninvasive interface) on the face of the patient. The flexible straps 12A, 12B, 14A, 14B have longitudinally spaced indexing holes 21 which selectively mate with outwardly-projecting retention posts 22 (or clips) formed with a top of the mask 18 to adjustably fit the mask on the face. Alternatively, the straps 12A, 12B, 14A, 14B may be adjustably attached to the ventilation mask 18 by any other suitable means, including slides, buckles, hook and loop fasteners, and the like. The mask 18 serves to interface a ventilator or other pressure support system with the airway of the patient so that a flow of breathing gas can be effectively administered to the patient.

Figure 2:
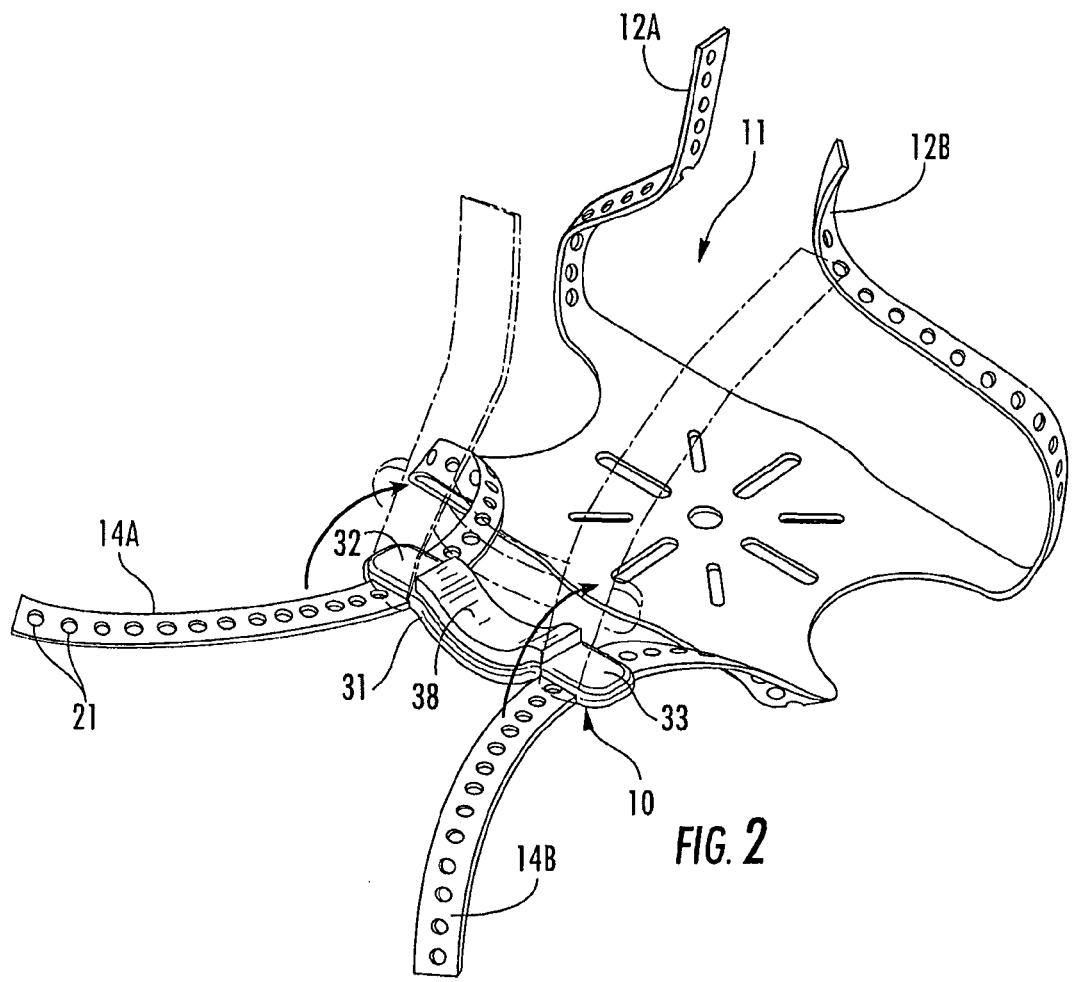
FIG. 2 is a perspective view of the headgear with the exemplary chin support carried on the flexible bottom straps.
Figure 3:
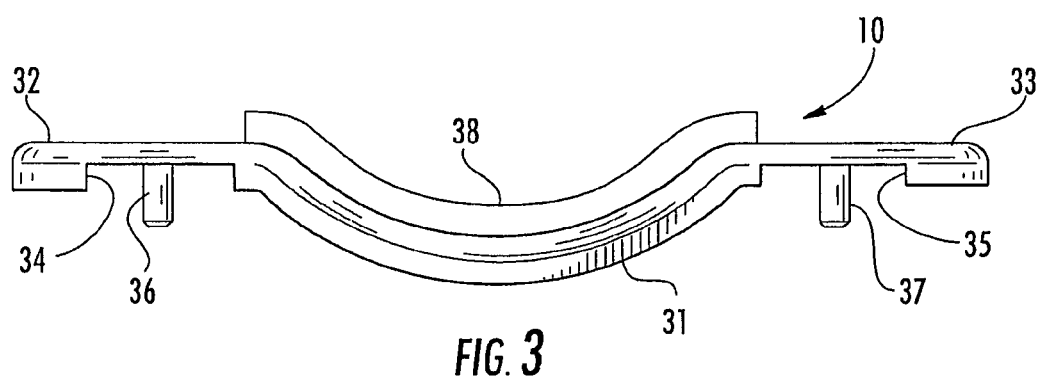
FIG. 3 is a side view of the exemplary chin support.

The present exemplary chin support 10 comprises a generally arcuate and substantially rigid chin cradle 31, and first and second substantially rigid collinear extensions 32, 33 formed at opposite ends of the chin cradle 31. When the ventilation mask 18 is worn by the patient, as shown in FIG. 1, the extensions 32, 33 are pulled by respective bottom straps 14A, 14B of the headgear 11 to urge the chin cradle 31 against the mandible of the patient. The simple extension at the atlanto-occipital joint allows the tongue to lift forward providing a patent airway for the spontaneously breathing patient under various forms of anesthesia. As best shown in FIGS. 2 and 3, the extensions 32, 33 may define respective strap grooves 34, 35 for receiving and positioning the flexible straps 14A, 14B, and respective outwardly-projecting retention posts 36, 37 designed to insert within selected indexing holes 21 of the straps 14A, 14B. The strap grooves 34, 35 and retention posts 36, 37 cooperate to retain the ergonomic chin support 10 in the selected location along the lengths of the bottom straps 14A, 14B, such that the chin cradle 31 remains properly located and aligned under the mandible to help maintain a patent airway during ventilation of the patient. A padded chin cushion 38 may be adhered to an inside of the arcuate chin cradle 31 to comfortably engage the skin of the patient during use of the ergonomic chin support 10. The chin cushion 38 may be constructed of any suitable material including gel, silicone, foam, rubber, and combinations of these materials. In one exemplary embodiment, the arcuate chin cradle 31 and extensions 32, 33 are constructed of plastic, and are integrally formed together (e.g., by molding) as a single homogenous unit.

Figure 4:
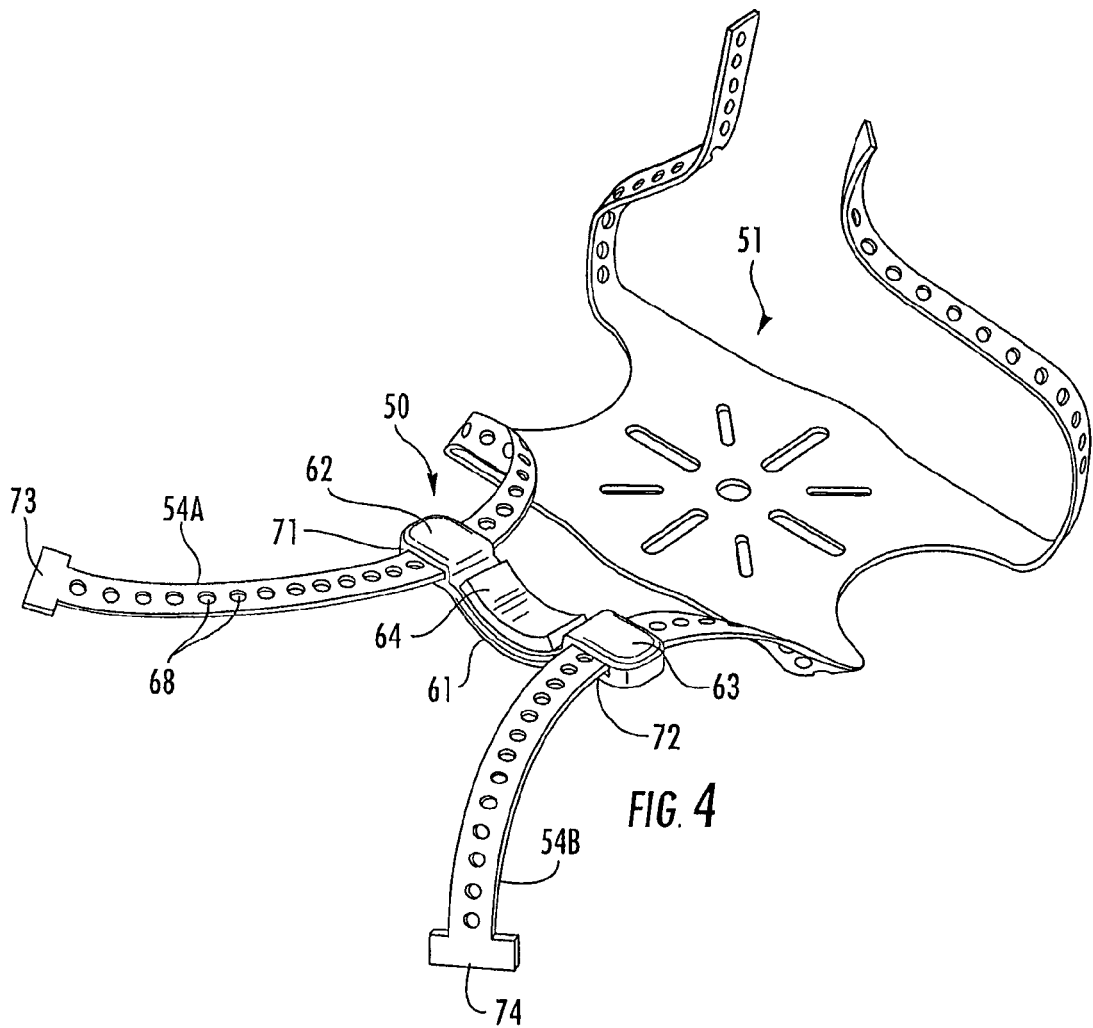
FIG. 4 is a perspective view of the headgear showing an alternative exemplary chin support carried by the flexible bottom straps.
Figure 5:
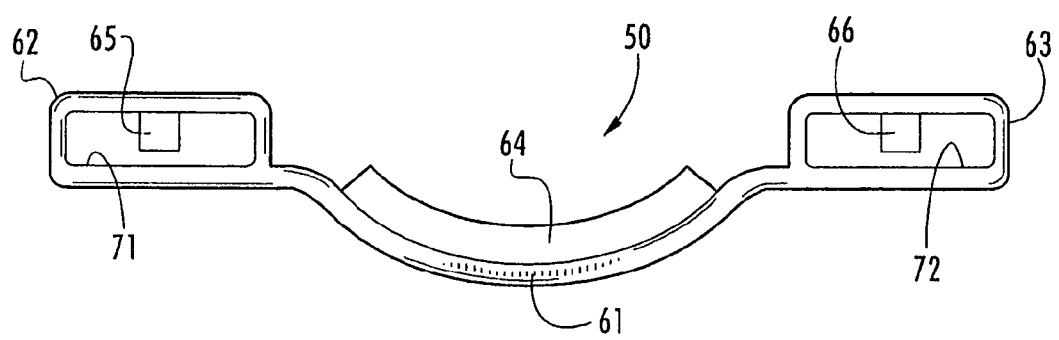
FIG. 5 is a side view of the alternative exemplary chin support.

A further exemplary embodiment of an ergonomic chin support 50 according to the present disclosure is shown in FIGS. 4 and 5. As previously described, the ergonomic chin support 50 is designed for use in combination with headgear 51 comprising pairs of top and bottom flexible straps 54A, 54B (only bottom straps shown). The exemplary chin support 50 comprises a generally arcuate and substantially rigid chin cradle 61, and first and second substantially rigid collinear extensions 62, 63 formed at opposite ends of the chin cradle 61. The chin cradle 61 may also include a separately attached chin pad 64. The extensions 62, 63 have outwardly-projecting retention posts 65, 66 designed to insert within selected indexing holes 68 of the straps 54A, 54B, as previously described, and may further define respective closed (or enclosed) rectangular slots 71, 72. The extensions 62, 63 slidably receive the flexible straps 54A, 54B through respective slots 71, 72, while the straps 54A, 54B may have enlarged end stops 73, 74 to inseparably couple the ergonomic chin support 50 and headgear 51.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under §112, 6th paragraph is not intended. Additionally, it is not intended that the scope of patent protection afforded the present invention be defined by reading into any claim a limitation found herein that does not explicitly appear in the claim itself.

We claim:

1. In combination with headgear comprising flexible straps adapted for locating a ventilation interface on a patient, an ergonomic chin support comprising:
   a generally arcuate and substantially rigid chin cradle;
   first and second substantially rigid and substantially collinear extensions formed at opposite ends of said chin cradle, and adapted for being pulled by respective straps of said headgear to urge said chin cradle against the mandible of the patient; and
   means for retaining said ergonomic chin support at a fixed location along respective lengths of said straps.

2. A combination according to claim 1, and comprising a chin cushion applied to said chin cradle.

3. A combination according to claim 2, wherein said chin cushion comprises a material selected from a group consisting of gel, silicone, foam, rubber, and combinations thereof.

4. A combination according to claim 1, wherein said first and second extensions comprise respective strap channels designed to receive respective flexible straps of said headgear.

5. A combination according to claim 4, wherein said means for retaining comprise respective retention posts formed with said first and second extensions within said strap channels, and wherein said flexible straps of said headgear define indexing holes adapted to selectively receive respective retention posts.

6. A combination according to claim 1, wherein said chin cradle and extensions are integrally-formed together as a single homogenous unit.

7. A combination according to claim 1, wherein said first and second extensions define respective closed strap slots receiving said flexible straps of said headgear therethrough, such that said ergonomic chin support is slidably disposed on respective lengths of said straps.

8. A combination according to claim 7, wherein said flexible straps comprise respective enlarged end stops adapted for holding said ergonomic chin support onto said headgear.

9. An ergonomic chin support for use in combination with headgear comprising flexible straps, said ergonomic chin support comprising:
   a generally arcuate and substantially rigid chin cradle;
   first and second substantially rigid and substantially collinear extensions formed at opposite ends of said chin cradle, and adapted for being pulled by respective straps of the headgear to urge said chin cradle against the mandible of the patient; and
   means for retaining said ergonomic chin support at a fixed location along respective lengths of the straps.

10. An ergonomic chin support according to claim 9, and comprising a chin cushion applied to said chin cradle.

11. An ergonomic chin support according to claim 10, wherein said chin cushion comprises a material selected from a group consisting of gel, silicone, foam, rubber, and combinations thereof.

12. An ergonomic chin support according to claim 9, wherein said first and second extensions comprise respective strap channels designed to receive respective flexible straps of the headgear.

13. An ergonomic chin support according to claim 12, wherein said means for retaining comprise respective retention posts formed with said first and second extensions within said strap channels, and adapted for selectively mating with indexing holes formed with respective straps of the headgear.

14. An ergonomic chin support according to claim 9, wherein said chin cradle and extensions are integrally-formed together as a single homogenous unit.

15. An ergonomic chin support according to claim 9, wherein said first and second extensions define respective closed strap slots adapted for receiving the flexible straps of the headgear therethrough, such that said ergonomic chin support is slidably disposed on respective lengths of the straps.

16. In combination with a ventilation interface, and headgear comprising flexible straps adapted for locating said ventilation interface on a patient, an ergonomic chin support comprising:
   a generally arcuate and substantially rigid chin cradle;
   first and second substantially rigid and substantially collinear extensions formed at opposite ends of said chin cradle, and adapted for being pulled by respective straps of said headgear to urge said chin cradle against the mandible of the patient; and
   means for retaining said ergonomic chin support at a fixed location along respective lengths of said straps.

17. A method for maintaining a patent airway during non-invasive ventilation of a patient, the method comprising:
   locating a ventilation interface on the patient;
   securing the ventilation interface using headgear comprising a chin cradle, flexible straps, and first and second substantially rigid and substantially collinear extensions formed at opposite ends of the chin cradle;
   using the flexible straps applied to respective extensions, pulling the chin cradle against the mandible of the patient; and
   selectively retaining the chin cradle at a fixed location along respective lengths of the flexible straps.

18. A method for maintaining a patent airway according to claim 16, wherein the step of selectively retaining comprises mating retention posts formed with respective extensions with complementary indexing holes formed with the flexible straps.

* * * * *